(12) United States Patent
Seres et al.

(10) Patent No.: US 11,806,267 B2
(45) Date of Patent: *Nov. 7, 2023

(54) OSTOMY PATIENT CARE SYSTEM AND METHOD

(71) Applicant: ConvaTec Technologies Inc, Las Vegas, NV (US)

(72) Inventors: Michael Seres, Radlett (GB); Karen Anaid Solis Gonzalez, La Puente, CA (US)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/644,456

(22) Filed: Dec. 15, 2021

(65) Prior Publication Data

US 2022/0249272 A1    Aug. 11, 2022

Related U.S. Application Data

(63) Continuation of application No. 16/263,555, filed on Jan. 31, 2019, now Pat. No. 11,291,577.

(60) Provisional application No. 62/625,904, filed on Feb. 2, 2018, provisional application No. 62/637,528, filed on Mar. 2, 2018.

(51) Int. Cl.
| | | |
|---|---|---|
| *G08B 5/00* | (2006.01) | |
| *H05B 39/00* | (2006.01) | |
| *H05B 41/00* | (2006.01) | |
| *A61F 5/44* | (2006.01) | |
| *G16H 20/40* | (2018.01) | |
| *G16H 80/00* | (2018.01) | |
| *A61F 5/445* | (2006.01) | |
| *G16H 40/67* | (2018.01) | |
| *G16H 10/60* | (2018.01) | |

(52) U.S. Cl.
CPC ............ *A61F 5/4404* (2013.01); *A61F 5/445* (2013.01); *G16H 10/60* (2018.01); *G16H 20/40* (2018.01); *G16H 40/67* (2018.01); *G16H 80/00* (2018.01)

(58) Field of Classification Search
CPC ....... A61F 5/4404; A61F 5/445; G16H 10/60; G16H 20/40; G16H 40/67; G16H 80/00
See application file for complete search history.

(56) References Cited

U.S. PATENT DOCUMENTS

| | | | |
|---|---|---|---|
| 8,398,603 B2 | 3/2013 | Thirstrup et al. | |
| 9,642,737 B2 | 5/2017 | Seres et al. | |
| 10,016,298 B2 | 7/2018 | Thirstrup et al. | |
| 10,500,084 B2 | 12/2019 | Hansen et al. | |
| 10,874,541 B2 * | 12/2020 | Seres | A61B 5/002 |
| 11,096,818 B2 * | 8/2021 | Thirstrup | A61F 5/445 |
| 11,291,577 B2 * | 4/2022 | Seres | G16H 40/67 |

* cited by examiner

*Primary Examiner* — Toan N Pham
(74) *Attorney, Agent, or Firm* — Taft Stettinius & Hollister LLP; Ryan O. White; Derek B. Lavender

(57) ABSTRACT

Systems and methods of providing post-operative ostomy patient care can include software and/or hardware that facilitates patient care personnel, such as a patient coach, providing remote patient care or coaching over a network to an ostomy patient. The care may be provided by specially trained former patients, nurses, or other care providers. The system can integrate sensor data from an ostomy device and inputs from the former patients, healthcare professionals, and/or device manufacturer in provide the post-operative care.

20 Claims, 9 Drawing Sheets

OSTOMY PATIENT CARE SYSTEM AND METHOD

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

The physical and emotional adjustment to wearing an ostomy bag can be difficult for new ostomy patients. These adjustments can include not only the short-term physical challenges involved with caring for the surgical site and operating the ostomy bag after an ostomy procedure, but also the more long-term physical and emotional challenges of learning to incorporate use of the ostomy bag in everyday living. These longer-term struggles can include everything from learning to empty the ostomy bag to overcoming fears of embarrassment and adjusting to an altered body image.

SUMMARY

Conventionally, limited patient care and training may be provided after an ostomy operation by the patient's clinical team. However, the ongoing day to day mental and physical difficulties of the transition to wearing an ostomy bag are difficult to address once the patient returns home. Thus, there is a need for patient care and coaching on an ongoing basis.

In some configurations, a system of providing post-operative care to an ostomy patient by a non-healthcare professional can include a non-transitory storage medium configured to store computer-executable instructions; and at least one hardware processor in communication with the non-transitory storage medium, wherein the at least one hardware processor is configured to: receive and process, over a network, ostomy data, wherein the ostomy data comprises data associated with use of an ostomy device by the ostomy patient, the ostomy data including at least a stomal output measurement; transmit, over the network, the processed ostomy data to a care provider device, the care provider device being operated by a non-healthcare professional; receive an input from the non-healthcare professional via the care provider device in response to the processed ostomy data; and transmit the input to the patient device.

In some configurations, the non-healthcare professional may have worn an ostomy device for a longer period than the ostomy patient.

In some configurations, the hardware processor can be further configured to receive, over the network, patient input data.

In some configurations, the patient input data can comprise information relating to at least one of food and/or liquids consumed by the user.

In some configurations, the hardware processor can be further configured to generate, based on the ostomy data and the patient input data, a monitored value.

In some configurations, the hardware processor can be further configured to generate an alert if the monitored value exceeds or falls below a threshold value.

In some configurations, the hardware processor can be further configured to transmit the alert to the care provider device.

In some configurations, the input can comprise a communication request from the care provider device to communicate with the patient device in response to the alert, the hardware processor further configured to transmit the communication request to the patient device and establish connection between the patient device and the care provider device.

In some configurations, the hardware processor can be further configured to transmit a request to a healthcare professional by the care provider device in response to the alert.

In some configurations, the hardware processor can be further configured to transmit a request to a patient treatment delivery service by the non-healthcare professional or the healthcare professional in response to the alert.

In some configurations, the hardware processor can be further configured to transmit a technical alert to a manufacturer of the ostomy device in response to the input, the input comprising a determination by the non-healthcare professional of a possible technical fault in the ostomy device.

In some configurations, the ostomy device can comprise an ostomy bag including one or more sensor layers disposed in, on, or between walls of the ostomy bag; and an electronics hub configured to transmit signals associated with the one or more sensor layers.

In some configurations, the ostomy device can comprise an ostomy wafer, the ostomy wafer including a plurality of sensors in communication with the electronics hub, the ostomy wafer including a patient facing surface and an ostomy bag facing surface that are opposite each other.

In some configurations, a method of providing post-operative care to an ostomy patient by a non-healthcare professional can include: receiving, over a network, and processing ostomy data, wherein the ostomy data comprises data associated with use of an ostomy device by the ostomy patient, the ostomy data including at least a stomal output measurement; transmitting, over the network, the processed ostomy data to a care provider device, the care provider device being operated by a non-healthcare professional; receive an input from the non-healthcare professional via the care provider device in response to the processed ostomy data; and transmit the input to the patient device.

In some configurations, the non-healthcare professional may have worn an ostomy device for a longer period than the ostomy patient.

In some configurations, the method can further comprise receiving, over the network, patient input data.

In some configurations, the method can further comprise generating, based on the ostomy data and the patient input data, a monitored value.

In some configurations, the method can further comprise generating an alert if the monitored value exceeds or falls below a threshold value.

In some configurations, the method can further comprise transmitting the alert to the care provider device.

In some configurations, the input can comprise a communication request from the care provider device to communicate with the patient device in response to the alert, the method further comprising transmitting the communication request to the patient device and establishing connection between the patient device and the care provider device.

In some configurations, the method can further comprise transmitting a request to a healthcare professional by the care provider device in response to the alert.

In some configurations, the method can further comprise transmitting a request to a patient treatment delivery service by the non-healthcare professional or the healthcare professional in response to the alert.

In some configurations, the method can further comprise transmitting a technical alert to a manufacturer of the ostomy device in response to the input, the input comprising a determination by the non-healthcare professional of a possible technical fault in the ostomy device.

In some configurations, the ostomy device can comprise an ostomy bag including one or more sensor layers disposed in, on, or between walls of the ostomy bag; and an electronics hub configured to transmit signals associated with the one or more sensor layers.

In some configurations, the ostomy device can comprise an ostomy wafer, the ostomy wafer including a plurality of sensors in communication with the electronics hub, the ostomy wafer including a patient facing surface and an ostomy bag facing surface that are opposite each other.

For purposes of summarizing the disclosure, certain aspects, advantages, and novel features of several embodiments have been described herein. It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as taught or suggested herein.

DETAILED DESCRIPTION

Introduction

Figure 1:
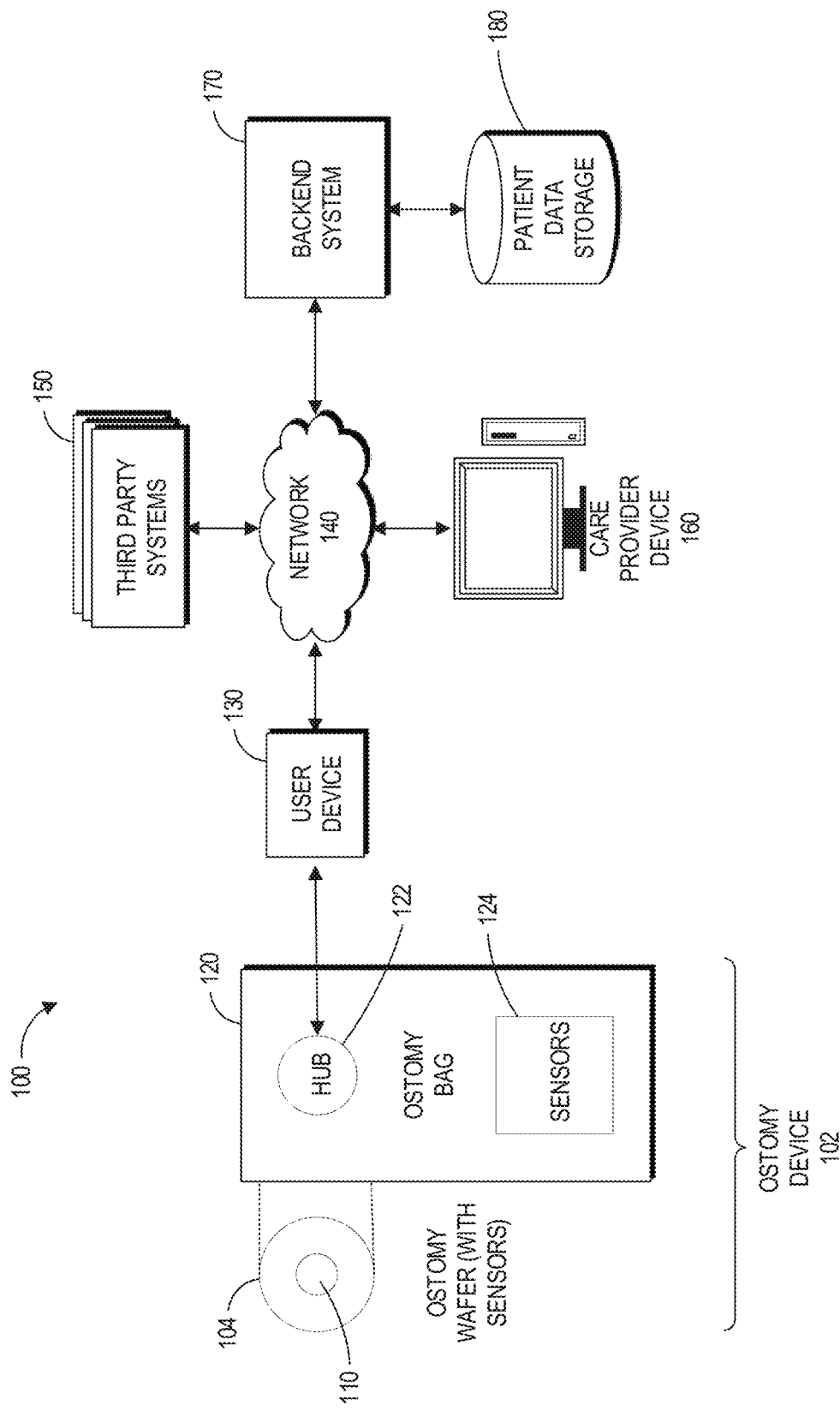
FIG. 1 illustrates an overview of an example ostomy monitoring environment.
Figure 2A:
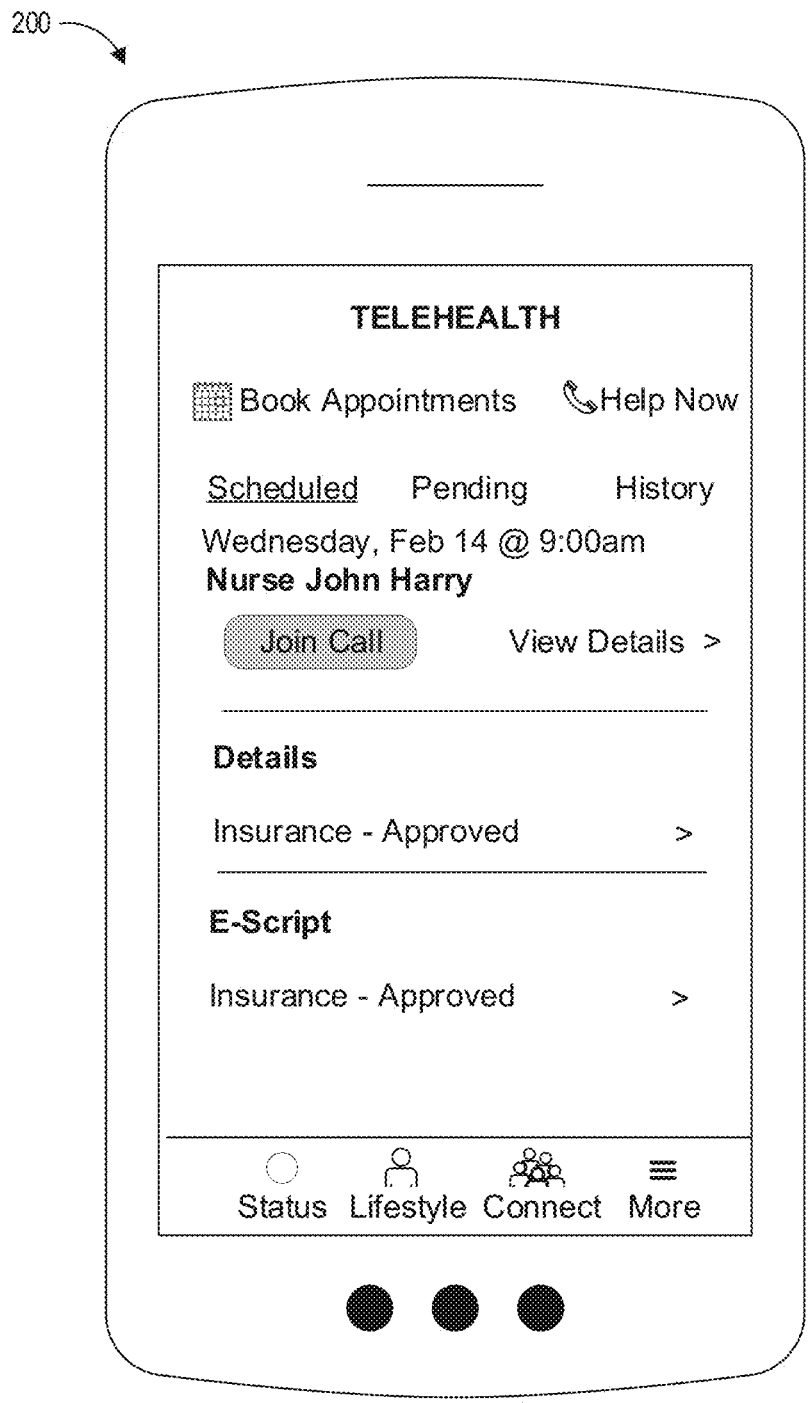
FIG. 2A illustrates an example view of a patient care interface for a patient to contact a care provider.
Figure 2B:
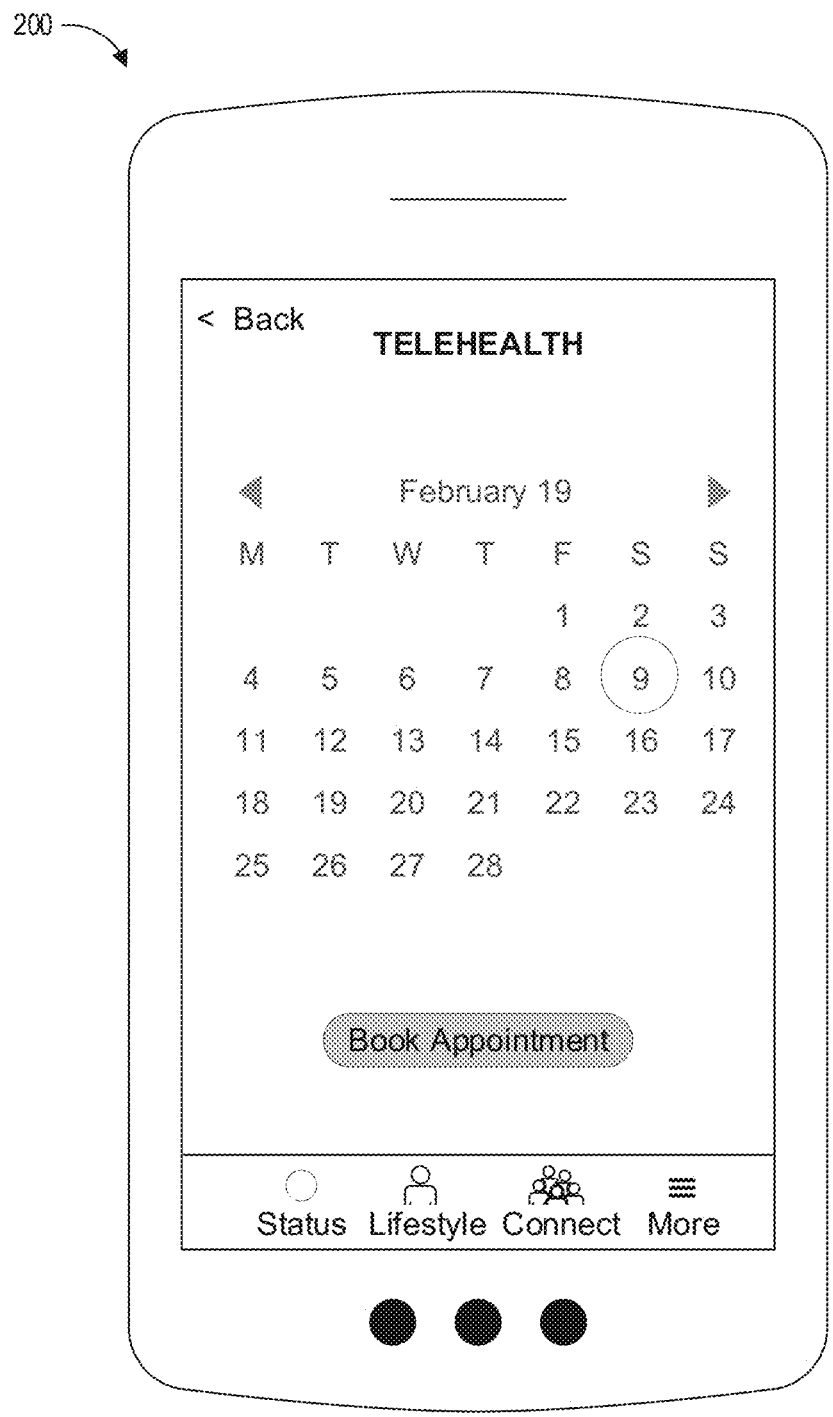
FIG. 2B illustrates an example view of a patient care interface for a patient or care provider to book an appointment.
Figure 2C:
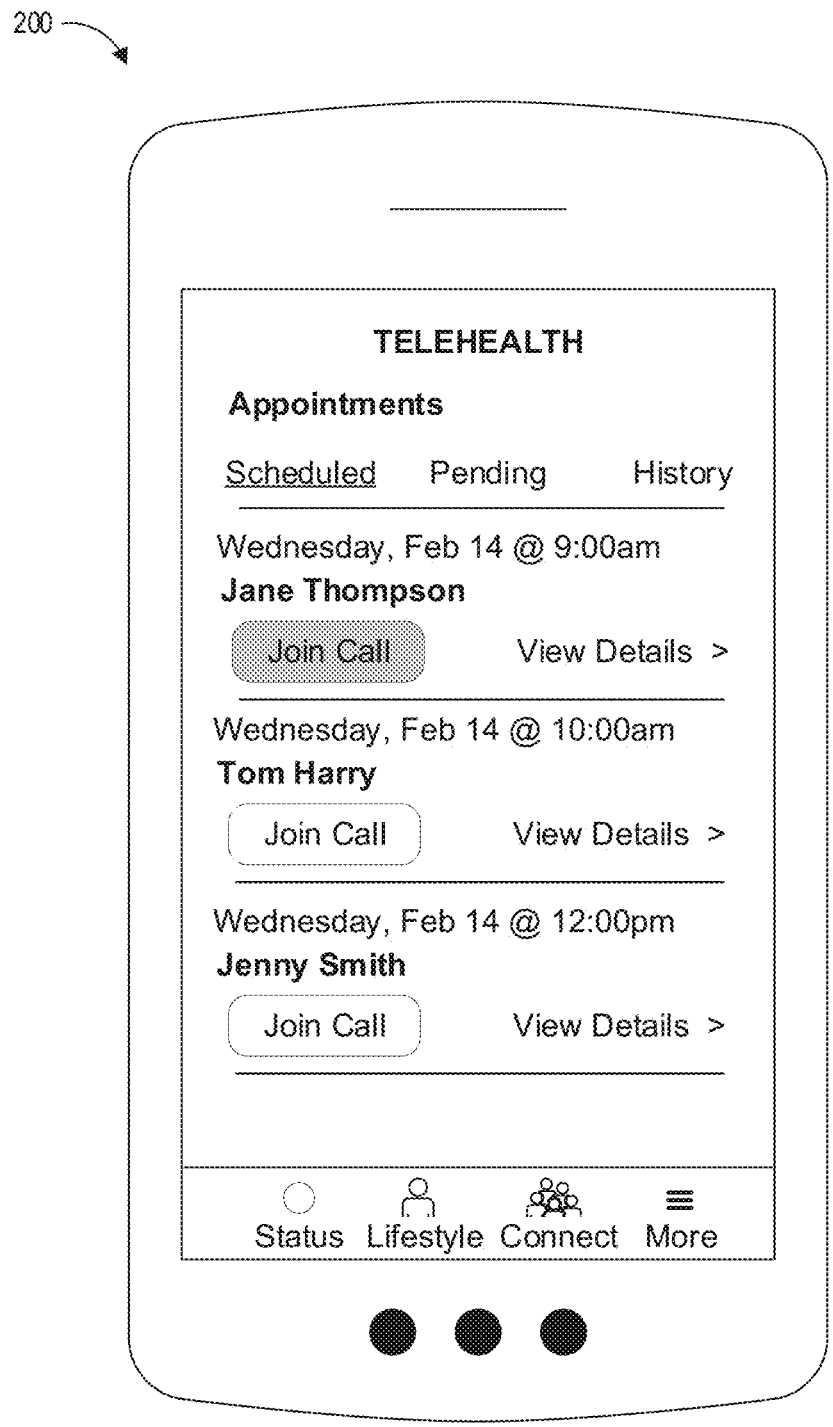
FIG. 2C illustrates an example view of a patient care interface for a care provider to manage appointments.
Figure 2D:
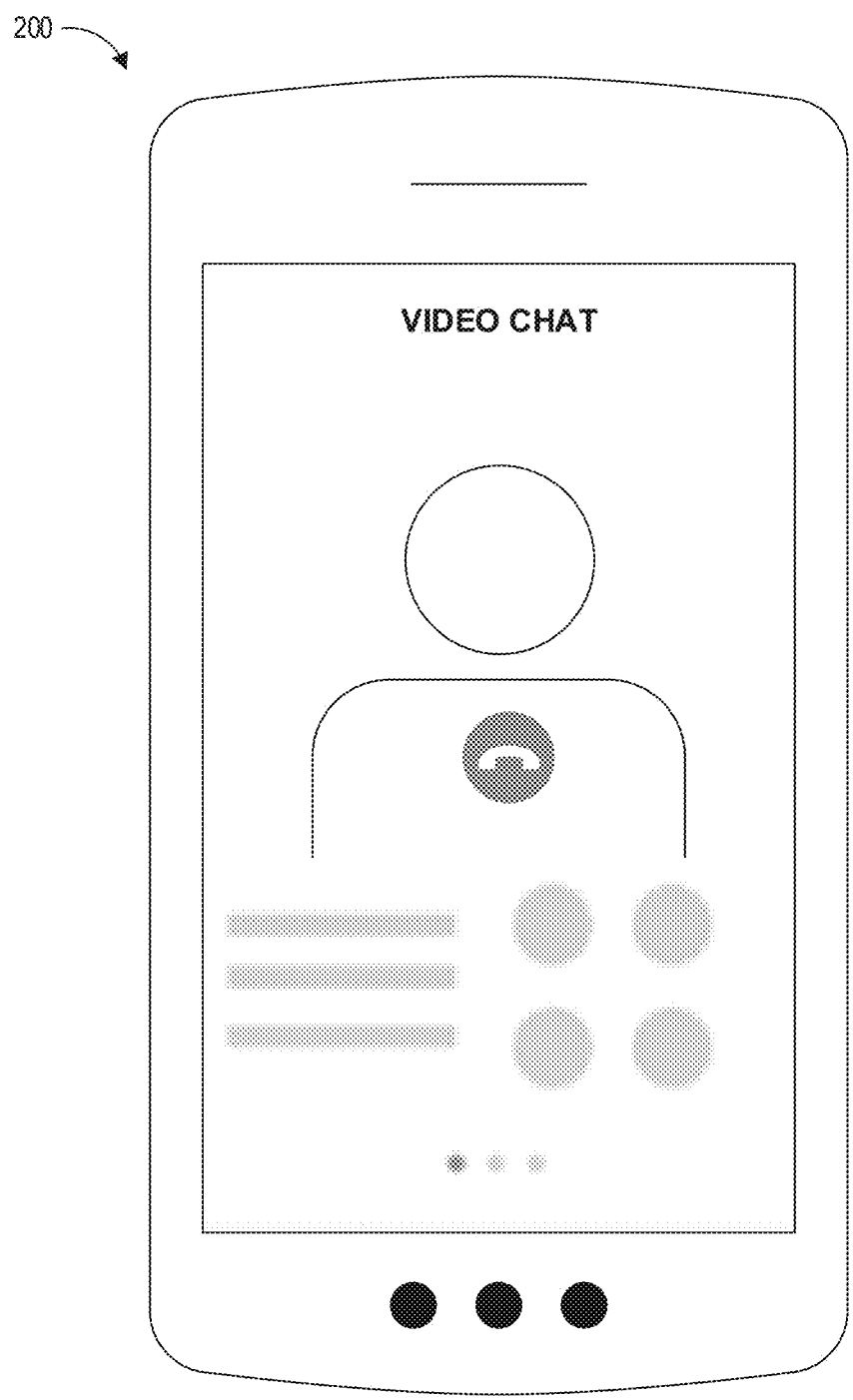
FIG. 2D illustrates an example view of a patient care interface for video chat between care providers and patients.

This disclosure describes embodiments of systems and methods for patient care. The systems and methods of patient care can include software and/or hardware that facilitates patient care personnel providing remote patient care or coaching over a network to a patient, such as an ostomy patient. For instance, this patient care may be provided for a period of time after an ostomy operation. One benefit of this patient care may be reduced readmissions of patients for subsequent surgery or care at a hospital. The patient care systems and methods can be examples of telehealth or telemedicine applications.

Ostomy patients, in particular, are chronic patients in that they must deal with the daily care and maintenance of an ostomy bag or pouch. Because of this ongoing need, patients may require ongoing care, especially in the weeks and months following an ostomy procedure when the patient is adapting to the new physical and emotional challenges of wearing an ostomy bag. An ostomy procedure involves significant changes in a person's appearance and daily living. These changes necessitate a certain adaptation of lifestyle, such as knowing when and how to empty or change an ostomy bag or pouch, can raise new medical concerns, such as effectiveness of time-released medication, and/or can create significant body image and relationship concerns.

This disclosure describes examples of systems and methods for remote monitoring and care of an ostomy patient, such as to help a new ostomy patient adjusting to wearing an ostomy bag. One example system can include connecting a patient with a social platform by which a case manager, patient coach, and/or clinical care provider can access data from sensors on the ostomy bag and/or wafer and interact with the patient to provide care, such as in response to the received data from the sensors. A patient coach can be an ostomy patient who has experience in wearing an ostomy bag, but is not a healthcare professional such as a nurse, physician, etc. The patient coach can be someone that has worn an ostomy bag for a duration longer than the new ostomy patient. The patient coach can also be someone that is still wearing an ostomy bag or has worn an ostomy bag in the past. A patient coach can also be someone that has assisted or has been educated by someone that has worn an ostomy bag. A patient coach can be someone who has been trained and become certified by an accredited body as a health coach.

The patient coach can analyze ostomy data received from the ostomy bag (such as from sensors on the ostomy bag and/or the ostomy wafer). The care can be in the form of technological support for the ostomy system, emotional support, and/or medical support. In case of a measured parameter in the ostomy data being outside a normal range, above or below a threshold, or otherwise indicating abnormality in the patient's stomal output or the stoma site (such as showing traces of blood, presence or absence of certain electrolytes, etc.), the patient coach can provide guidance (which can be technical and/or emotional support) to the new patient, determine whether other explanations exist for the abnormalities, refer the case to a healthcare professional for diagnosis, alert an ostomy device manufacturer of possible malfunction of the device, and/or ordering delivery of treatment (for example, fluid, antibiotics, and the like) to the new patient in response to the analysis of the ostomy data. Knowledge of experience from the patient coach, who may better understand the needs of the new patients, can advantageously offer emotional support and a possibility to reduce the learning curve of the new patient (which may be more real-time and more readily available than visiting a healthcare professional) in areas of ostomy self-care, ostomy supplies, social interaction, job, school, or any activity integration and self-knowledge to reduce or prevent health complications. The availability of an available healthcare professional and/or treatment delivery service, if needed, may help decrease unplanned hospital visits during the immediate post discharge period. The care provided to the new ostomy patient can take into account real-time patient data and/or allow more patient-specific decisions.

The systems and methods for patient care described herein can be implemented with any medical device. For example, the systems and methods may be implemented with an ostomy device. One such example of an ostomy device that may be used with the features described herein is the ostomy device described in U.S. Pat. No. 9,642,737, titled "Portable Level Sensor," issued May 9, 2017, the disclosure of which is hereby incorporated by reference in its entirety. Another example of such a device is described in U.S. patent application Ser. No. 16/184,764, filed Nov. 8, 2018, titled "OSTOMY MONITORING SYSTEM AND METHOD," the disclosure of which is hereby incorporated by reference in its entirety. Additionally, the ostomy device discussed below with respect to FIG. 1 may also implement the patient care features.

Overview

An ostomy bag can be a medical bag that collects human waste (either stools, urine, or both) from patients who cannot excrete waste naturally due to medical issues, which include, among others, cancer, trauma, inflammatory bowel disease (IBD), bowel obstruction, infection, and fecal incontinence. In such cases, a surgical procedure is performed whereby a waste passage is created. This waste passage can be the ureter (called an urostomy), the small bowel or ileum (called an ileostomy, part of the small intestine) or the large bowl or colon (called a colostomy, part of the large intestine), which may be diverted to an artificial opening in the abdominal wall, thus resulting in part of the specific internal anatomy, to lie partially outside the body wall. This procedure can be referred to as an ostomy, and the part of the waste passage which is seen on the outside of the body can be referred to as a stoma.

Ostomy patients can have unique challenges following an ostomy procedure. For example, in the weeks and months following the procedure, ostomy patients must learn how to care for the area around their stoma, learn the process of changing and emptying their ostomy bag, learn about medical complications with having a stoma, and/or learn to adjust their planning and lifestyle around being able to change and empty their ostomy bag when necessary. Some of these skills can be taught by clinicians (such as nurses) post-operatively, but many patients have ongoing questions and concerns regarding these adjustments that require continuing clinical care. Similarly, there are many emotional challenges involved with learning to live with a stoma. In particular, the stoma itself constitutes a physical change to the patient's body that requires an emotional adjustment. With this change, many patients are confronted with a significant change in body image with the stoma and may present with emotional fears regarding, for example, physically taking care of the stoma, ostomy bag leakage, traveling with an ostomy bag, and/or the impact of the stoma on the patient's personal relationships. Treating theses emotional challenges requires ongoing care to properly address.

Ongoing patient care can be provided via a social platform that connects patients with care providers. The care providers may be a clinician and/or a trained patient coach or "champion," such as a more seasoned ostomy patient. The platform may receive information from an ostomy monitoring system, which can include a smart ostomy bag (or "smart bag") and/or wafer such as described in U.S. patent application Ser. No. 16/184,764 and include patient and care provider interfaces that allow a patient to view and upload relevant information. A care provider can monitor and provide care to a patient via the platform. Access to the platform may come included with the smart bag or be granted through a subscription service.

An example smart bag and/or wafer can have integrated sensors that can track one or more in-situ physical events inside the bag. These events can include volumetric analysis, flow rate, physical phase of the effluent, viscosity of the effluent, possible skin irritation, leakage occurrence around the stoma and saturation of the hydrocolloid, and/or the like. The smart bag can also track more detailed clinical/analytical metrics of the bag such as electrolytic measurements, pH, and other markers.

An example smart bag may also include one or more wireless transmitters that transmit data from the ostomy wafer and/or ostomy bag to another device, such as a hub, a user device, a clinician device, and/or a back-end system. For example, the ostomy wafer and/or the ostomy bag can wirelessly transmit data to a hub coupled to the ostomy bag, and the hub can transmit the received data to a back-end system (such as cloud servers). A user device (for example, a smartphone or tablet used by the patient and/or the patient coach) can download the data and other information from the remote server.

A mobile application and/or web site can be provided to patients and/or the patient coaches, which can include a platform of different trackers such as food and hydration trackers. With the application optionally being able to record metrics such as diet and hydration (via user interaction and trackers within the app) and the bag sensor(s) able to indicate the volume in the bag, this integrated platform can help to provide early signs of inflammation, dehydration, dietary issues, or even GI dysfunction in patients. Dehydration can be a significant metric because it is one of the most common reasons why patients are readmitted into the hospital in the first three months following ostomy surgery. Thus, providing features that can help patients and/or the patient coaches become aware of the output in the ostomy bag can enable patients and/or the patient coaches to better monitor and prevent dehydration, improving quality of care and life while at the same time potentially reducing the likelihood and/or extent of post-operative care, such as due to in hospital re-admissions following initial stoma surgery.

The platform may include an interface for patients and care providers to communicate and for care providers to provide care and coaching. The interface may provide various means of establishing communication between the patient and care provider. For example, the patient may be able to use an interface to contact a care provider by calling them through the interface. Alternatively, they may schedule an appointment to meet in person or via the application through a calendar application. The care provider can also call the patient directly through the application periodically and/or based on the ostomy data received from the patient's ostomy device. The care providers can also establish, view, and rearrange their schedule of appointments.

Care providers may include nurses, psychologists, doctors, and more experienced ostomy patients (patient coaches) that are trained to provided care and support. The patient coaches may be ostomy patients that are recruited through social media or by doctor recommendation to provide emotional and educational support to the new patient. The patient coaches may go through a certification process and can provide coaching and create content on the platform on a regular basis (for example, at least 4, 5, 6, 8, or more articles per year). The patient coaches may serve as the first person that the patient interacts with when they have a question and may redirect medical or severe emotional issues to an appropriate professional. The patient coach may also have access to data from a patient's smart bag and/or wafer and be notified of alerts generated by the smart bag. For example, the smart bag may determine that the patient is dehydrated. The patient coach may contact the patient to determine if the alert is correct and whether the patient needs to be evaluated and treated by a professional clinician. The patient coach and/or the professional clinician may order delivery of treatment to the patient. The patient coach may identify possible malfunctioning of the ostomy device based on the data. The patient coach may also provide technical support in the form of teaching the patient how to use their ostomy device.

A patient may be paired with a patient coach using a pairing algorithm (such as based on location, gender, age, type of ostomy surgery received, and/or the type of support needed by the patient, for example, technical support, emotional support, and/or others), or select a patient coach based on any one or combination of the aforementioned factors. When multiple patient coaches qualify, the patient may be allowed to look through and select from the list of qualified coaches. One patient can be paired with more than one patient coaches, for example, different patient coaches may focus on different types of support. One patient coach can be paired with one or more patients.

The type of care provided by the care providers can be in a variety of medical and lifestyle arenas, including in the areas of ostomy self-care, ostomy supplies, social interaction, job, school or any activity integration and self-knowledge to prevent health complications. In addition to being available to answer questions and address concerns, patients may be contacted periodically by care providers to follow up with the patient regarding their recovery from the ostomy procedure and transition into life with a stoma. In the days and weeks following an ostomy procedure, this contact may occur multiple times a week. After a few months, this contact may occur less frequently, for example moving down to every other week and then on an as needed basis. Different types of care providers may contact the patient at different periodic intervals. For example, a nurse care provider may contact the patient more frequently early on after the stoma procedure to ensure that the patient is properly healing. A psychologist care provider may contact the patient on a regular schedule for a period of time following the procedure, such as weekly or biweekly, and then on an as needed basis. A patient coach may interact with the patient weekly, such as through a support group, and/or interact with the patient on an as needed basis. An intelligence (AI) service can also optionally be available. The AI service can be made available to the patient, including when the patient coach or healthcare professionals are not available. The AI service can be equipped with natural language processing and can be trained to answer educational questions, such as commonly asked questions from ostomy patients.

Example Ostomy Monitoring System

In FIG. 1, an overview of an ostomy monitoring environment 100 is provided in which an ostomy device 102 used by a patient may be monitored. In this environment 100, the ostomy device 102 is shown in communication with a user device 130. The user device 130 is shown in communication with other devices over a network 140. These other devices include, in the example shown, a clinician device(s) 160, a backend system 170, and third-party systems 150. The ostomy monitoring environment 100 depicts an example environment, and more or fewer devices may communicate with the ostomy device 102 in other systems or devices. The ostomy monitoring environment 100 can enable a user and others (such as clinicians) to monitor various aspects related to the user's ostomy device 102, such as ostomy bag fill, leaks, and skin irritation.

The ostomy device 102 is shown having two main components, an ostomy wafer 104 and an ostomy bag 120.

The ostomy wafer 104 can be an adhesive pad, flange, or the like that attaches to a patient's skin around a stoma 110. The stoma 104 can include, for example, an aperture or hole in a patient's abdomen (or other location) resulting from a colostomy, ileostomy, urostomy, or other similar medical procedure. The ostomy bag 120 can removably attach to the ostomy wafer 104. The ostomy bag 120 can receive and store any output (e.g., effluent) from the stoma 110. Once the ostomy bag 120 has reached its designed capacity, the patient (or care provider) may remove the ostomy bag 120 from the ostomy wafer 104, discard or empty it, and attach a new ostomy bag 120 (or clean and reattach the old ostomy bag 120). In another example, the ostomy bag 120 is provided or sold together with the ostomy wafer 104 as a single device, with the ostomy wafer 104 integrally formed with the ostomy bag 120. The ostomy bag 122 collects human waste (both stools and urine) from patients who cannot excrete waste naturally due to medical issues, which span from cancer, trauma, inflammatory bowel disease, bowel obstruction, infection, and incontinence. In such cases, a procedure can be performed where a waste passage is created (colostomy, ileostomy, or urostomy) and diverted to a section of the abdominal wall. This ostomy bag 122 can be made of non-porous sterile plastic materials such as, but not limited to, polyvinyl chloride, polyethylene, ethylene vinyl acetate, polypropylene, and copolyester ether. An ostomy bag 122 can be a medical bag that has a carbon filter port or gas sensor placed on the port. The carbon filter port and can be placed on the bag to allow gas to escape to prevent ostomy bag 120 rupture. The gas sensor can detect the pungency of the gas to determine the status of the user's gut.

The sensors of the ostomy wafer 110 can be disposed in a sensor layer (described in detail below) that generally or partially has a similar or the same shape outline as the ostomy wafer 110. For example, if the ostomy wafer 110 is shaped like a donut or annulus, the sensor layer may include a generally annular shape. The sensor layer can also have a shape that differs from the general shape of the wafer 10, such as a partially annular or partial ring shape.

The ostomy wafer 110 can be a flexible sheet with one or more layers, and optionally, multiple layers including one or more sensor layers. One or more of the layers of the ostomy wafer 110 may include one or more of the following sensors: temperature sensors (such as thermistors), capacitive sensors, flex sensors, odor sensors, microfluidic sensors, leak sensors, combinations of the same, or the like.

The sensors can detect the output of the stoma 104. The sensors 104 can sense the phase and/or constituents of the effluent or output of stoma 104. Temperature sensors can be used to determine whether there is inflammation at the site of the stoma or if there is a leak. Temperature sensors may also be used to determine how much gas is in the bag by detecting the phasing of the constituents. A capacitive sensor may serve as a fallback to a temperature sensor to determine if there is a leak. A capacitive sensor may be used to detect moisture, thus may also be used to determine a level of the effluent in the ostomy bag. If microfluidic sensors are used, the sensors can be used to detect electrolytes or inflammation markers within the constituents. This data can be used to show the user what he or she needs to intake or do to obtain a healthy balance. An odor sensor can determine whether there is bacterial growth in the gut. An inertial measurement unit ("IMU") sensor, a form of positional indicator (such as an accelerometer, gyroscope, etc.), can be integrated. An optical sensor or camera may also be integrated where the sensor looks down over stoma and into the bag in order to detect a degrading stoma, blood in the stool, etc. A pH sensor may also be integrated as well to determine the acidity of the constituents of the bag.

The ostomy wafer 110 can be any size. The size of the ostomy wafer 110 can depend on the type of stoma that the wafer 110 is used with. For example, a colostomy stoma can be larger than a urostomy stoma. Thus, the ostomy wafer 104 can be sized larger for some colostomy stomas than for some urostomy stomas. The ostomy wafer 110 can be in any of a variety of different shapes. The ostomy wafer 110 can have a generally annular shape, such as a ring, donut, or the like. Or, the ostomy wafer 110 can have a more rectangular of square shape (optionally with rounded corners).

A donut shape or partial ring shape can be used for the sensor layer of the ostomy wafer. These shapes may have a user customizability feature by facilitating cutting the sensor layer to better fit the stoma 104. Either design may also have a flexible bottom which aids in flexibility and which equates to better user comfort.

The flexible sheet can be layered in structure to encapsulate the sensors. Encapsulation ensures or attempts to ensure that the temperature sensors are held in position in the flexible sheet and that they are protected from corrosion by the external environment. As an alternative to encapsulation, the temperature sensors may be protected from corrosion by a coating, such as a conformal coating. Some systems can have at least one temperature sensor in the second region of the flexible sheet that is protected by a conformal coating.

The ostomy wafer 104 can have an adhesive side that adheres to skin around a stoma 110 and/or directly to the stoma 110. The adhesive can be a double-sided adhesive. The adhesive may be a hydrocolloid adhesive.

The ostomy wafer 110 and the ostomy bag sensor 124 can collect patient data and can transmit the data either directly or via a hub 122 to a mobile device, such as a user device 130. The data can then be sent to a network 140, third-party systems 150, a clinician device 160, a backend system 170, or to patient data storage 180. The transmission may occur via a wireless transmitter or via wires. Wireless transmission may use near-field communication a combination of NFC and Bluetooth. The wireless transmitter may be incorporated into the hub 122 or may operate separately. In one configuration, the hub 122 can have a wireless transmitter. The wireless transmitter may include a Bluetooth transmitter, a radio transmitter, or a Wi-Fi transmitter. The Bluetooth transmitter may include a Bluetooth module and/or a Bluetooth low energy (BLE) module. A Bluetooth module may be, but is not limited to, a Bluetooth version 2.0+EDR (Enhanced Data Rates) module. A Bluetooth low energy module may be a Bluetooth module such as, but not limited to, a Bluetooth version 4.0 (Bluetooth smart), a Bluetooth version 4.1, a Bluetooth version 4.2 or a Bluetooth version 5. The Bluetooth sensor module may include a Bluetooth module using IPv6 Internet Protocol Support Profile (IPSP). The Bluetooth module and/or the Bluetooth low energy module may use or include newer versions than the versions described above.

The hub 122 can be in various positions on the device 102. The hub 122 can be placed in many areas on the ostomy bag 120. The hub 122 can be placed in the front, the back, next to a carbon filter (not shown), or the like. The hub 122 can also be placed in a pocket on the ostomy bag 120 or the hub 122 could be a replaceable feature on ostomy bag 120. The hub 122 can also come in different forms. When the hub is removed from the ostomy bag 120 it can use previous collected data and carry over that data to the next subsequent ostomy bag 120 that it is placed upon. This can increase patient data feedback and save money for the user by not throwing away hubs 122 so frequently. The ostomy bag 120 may also have a flexible sheet sensor 124 including thermal sensors that can compare the temperature in a first fusion of a flexible sheet with the temperature in the second region of the flexible sheet. The hub 122 may also include a processor. In order to preserve battery life, the wireless transmitter may be switchable to an active mode and idle mode.

The user device 130 can be any device with a processor and a wireless receiver that can communicate with the hub 122. For example, the user device 130 can be a phone, smart phone, tablet, laptop, desktop, audio assistant or smart speaker (such as an Amazon Echo™, Google Home™, Apple HomePod™, or the like), television, or the like that may pair automatically to the wireless transmitter and may include a mechanism that advises the user of the subsistence of a wireless link between the wireless receiver and the wireless transmitter. The user device 130 may have software and algorithms to process the data to show the user the status of the fill of the bag, the nearest restroom, nearest sources of electrolytes, nearest source of food, patterns and contents of discharge, hydration levels, possible skin irritation, recommendations to improve the user's condition, combinations of the same, or the like. The user device 130 may also transmit the data wirelessly to a network 140. The network 140 can be a local area network (LAN), a wide area network (WAN), the Internet, an Intranet, combinations of the same, or the like.

The third-party systems 150 can be data processing tools/features, smart home devices, backend servers for audio assistance, fitness trackers, personal health monitors, or any third-party systems that can use or manipulate the data collected by the device 102. These third-party systems 150 may also include algorithms and software to calculate and process the data.

Third party systems 150 and smart home devices can fetch or receive data from the device 102 to announce reminders or alerts for the user such as to empty the bag, change the bag, change the hub, intake or stop in-taking certain types of food, intake water, and/or providing periodic check ins. Other third-party systems may use data collected from all users to create a better feedback system or to identify patterns within a demographic of ostomy patients and/or bag users.

The care provider device 160 can be a data processing system or monitoring program used by a clinician. The care provider 160 also includes a data processing system or monitoring program used by a patient coach. These care provider devices 160 may fetch or receive data from the device 102 to provide a remote clinician with information which may assist the clinician to diagnose the user, recommend actions to the user, or function as an augmented reality system for the clinician and/or the patient coach. These care provider devices 160 may also include algorithms and software to calculate and process the data.

The backend system 170 can also use algorithms and software to perform data processing. For instance, the backend system 170 can process any data received from the sensors on the wafer and/or bag and return information based on that processing to the user device 130 or other devices. Another optional feature is an inclusion of a patient data storage system 180. From here the backend system can send the data to the patient data storage wirelessly, or the patient data storage can access the data from the network 140.

Algorithms and software can show when the user should replace the bag, alert the user when the bag is nearly full or when there is a leak in the bag. Software features include, but are not limited to, the nearest restrooms within the user's radius, the volume of the user's pouch, alarms for different fill levels, a hydration and electrolyte tracker which calculates the user's recommended daily hydration goal with an algorithm. The hydration and electrolyte software can notify the user based off their effluent constituency, what his or her dietary needs may be throughout the day, etc.

Example Patient Care Interfaces

FIGS. 2A-2D depict example patient care interfaces 200 that, as shown, provide patients (e.g., FIG. 2A, 2B, 2D) and care providers (e.g., FIG. 2B, 2C, 2D) with an interface for communicating and providing care and coaching. Patient user interfaces may be displayed on the user device 130 of FIG. 1. Similarly, care provider user interfaces may be displayed on the care provider device 160 or on another user device (like the user device 130). The care provider user interfaces need not be operated by a clinician but can be operated by a trained patient coach or "champion," such as a more seasoned ostomy patient who is not a healthcare professional. The backend system 170 can include software that facilitates communications between the user device 130 and the clinician or care provider device 160.

The interface includes various means of establishing communication between the patient and care provider. For example, the patient may be able to use the interface to contact a care provider by calling them through a video chat feature (e.g., FIG. 2D) of the interface. Alternatively, they may schedule an appointment (e.g., FIGS. 2A, 2B) to meet in person or via the application through a calendar application. The care provider can also call the patient directly through the application. The care provider can also establish, view, and rearrange their schedule of appointments (e.g., FIG. 2C).

Each of the user interfaces shown includes one or more user interface controls that can be selected by a user, for example, using a browser or other application software (such as a mobile application). Thus, each of the user interfaces shown may be displayed for presentation by electronic hardware as graphical user interfaces, which may optionally include a browser, or any other application software installed thereon that displays the user interfaces.

The user interface controls shown are merely illustrative examples and can be varied in other embodiments. For instance, any of the user interface controls shown may be substituted with other types of user interface controls that provide the same or similar functionality. Some examples of user interface controls that may be used include buttons, dropdown boxes, select boxes, text boxes or text fields, checkboxes, radio buttons, toggles, breadcrumbs (e.g., identifying a page or interface that is displayed), sliders, search fields, pagination controls, tags, icons, tooltips, progress bars, notifications, message boxes, image carousels, modal windows (such as pop-ups), date and/or time pickers, accordions (for example, a vertically stacked list with show/hide functionality), and the like. Additional user interface controls not listed here may be used.

Further, user interface controls may be combined or divided into other sets of user interface controls such that similar functionality or the same functionality may be provided with very different looking user interfaces. Moreover, each of the user interface controls may be selected by a user using one or more input options, such as a mouse, touch screen input (e.g., finger or pen), or keyboard input, among other user interface input options. Although each of these user interfaces are shown implemented in a mobile device, the user interfaces or similar user interfaces can be displayed by any computing device, examples of which are described above.

Example Patient Care Providers

Care providers may be clinicians, such as nurses, doctors, and psychologists, or patient coaches. Clinicians may provide professional support as needed. This support may include contacting the patient on a set schedule for a period of time after discharge to ensure recovery from the ostomy procedure or be available to the patient to contact on an as needed basis. Patient coaches may provide lifestyle, educational, and ostomy device related support.

The patient coaches may be experienced ostomy patients that are specially trained to provide coaching to new ostomy patients. A patient coach may be recruited through other patient coaches, social media, or by clinician recommendation. The patient coaches may be paid to provide social media content, create educational material, answer questions regarding life with an ostomy bag, give lifestyle advice, provide emotional support to new ostomy patients using the platform, and/or act as a preliminary interpreter of patient and ostomy bag data. The patient coaches' protocols may determine whether any abnormalities in the ostomy bag data would require attention from a clinician and/or an ostomy device manufacturer.

As part of their duties, a patient coach may be tasked with communicating with a patient, or multiple patients, on a regular basis. This communication may be done by running a support group through the patient user interface by which other ostomy patients can interact with each other to provide encouragement, comfort, and advice. This communication may involve having set hours by which a patient can contact the patient coach with questions or for needed emotional support. The patient coach may communicate with the patient by appointment. The appointments may be managed through the patient care interface.

Example Patient Care Alerts

The patient coach may be notified of alerts associated with the ostomy device 102 or patient care interface 200. The patient coach may then review the alerts and determine what, if any, further action needs to be taken (for example, pursuant to preset protocols) to address the alerts. These alerts can include technical alerts associated with the ostomy device or other alerts associated with use of the ostomy device.

Technical alerts can include when sensors 124 may be disconnected or malfunctioning, when there is an inability of the user device 130 to connect with the hub 122, or the like. In the case of technical alerts, the patient coach may contact the patient to attempt to determine the source of the alert and propose a solution to the problem, if feasible. For example, the alert may be that the ostomy device 102 has not connected to the user device 130 after a set period of time, such as a number of hours or days. The patient coach may contact the patient to determine if the ostomy device 102 is properly connected. The patient coach may determine that a battery associated with ostomy device 102 has been discharged and requires recharging. The patient coach can then walk through the recharging process with the patient. In other embodiments, the technical alert may be that a sensor is not transmitting data. The patient coach may contact the patient to determine if the ostomy device 102 is properly connected. Where further technical assistance is necessary, the device manufacturer may be contacted. The device manufacturer may directly receive a technical alert. The device manufacturer may then contact the patient to determine if assistance is necessary or if the device is defective.

Figure 3A:
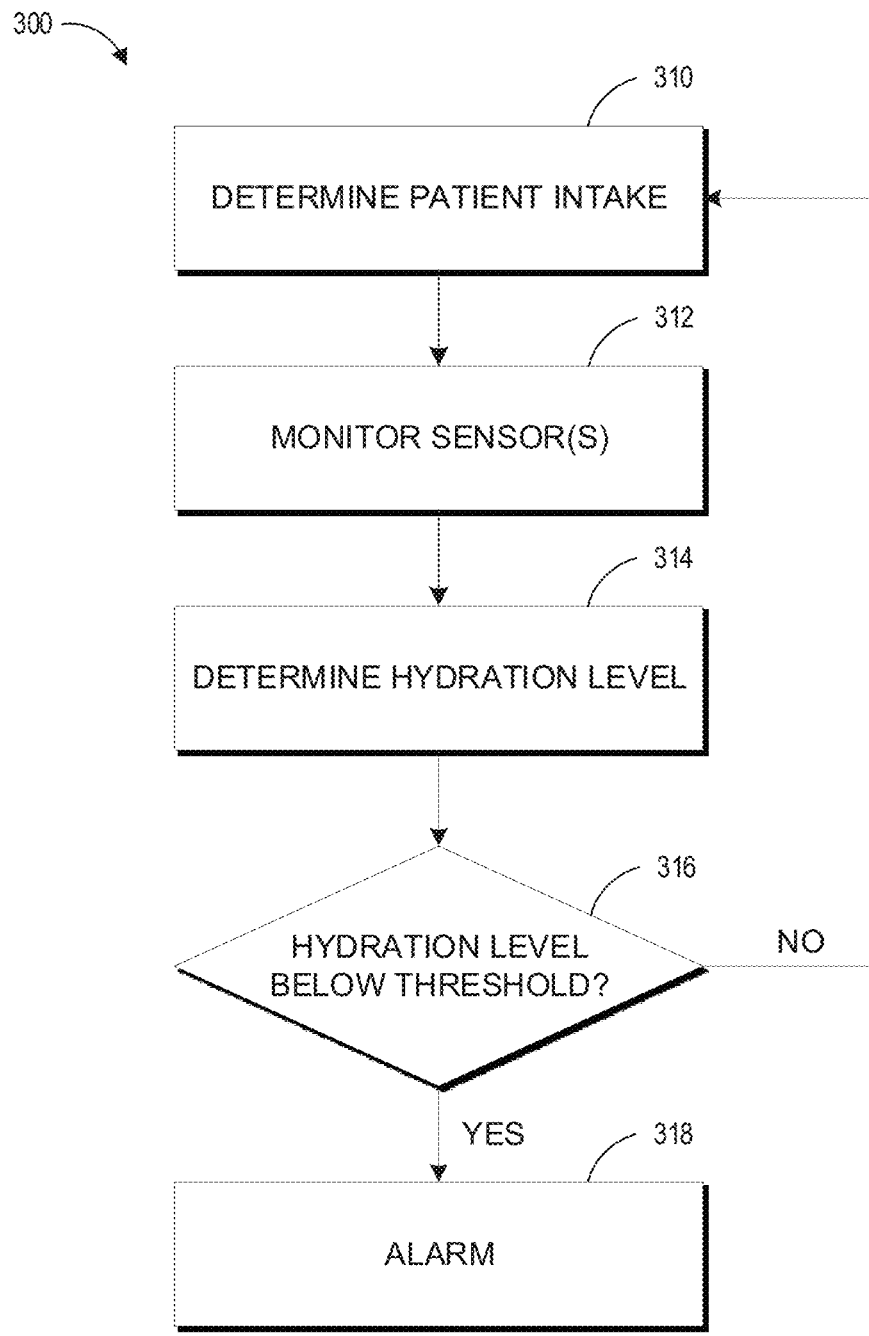
FIG. 3A illustrates an example patient care alert process.
Figure 3B:
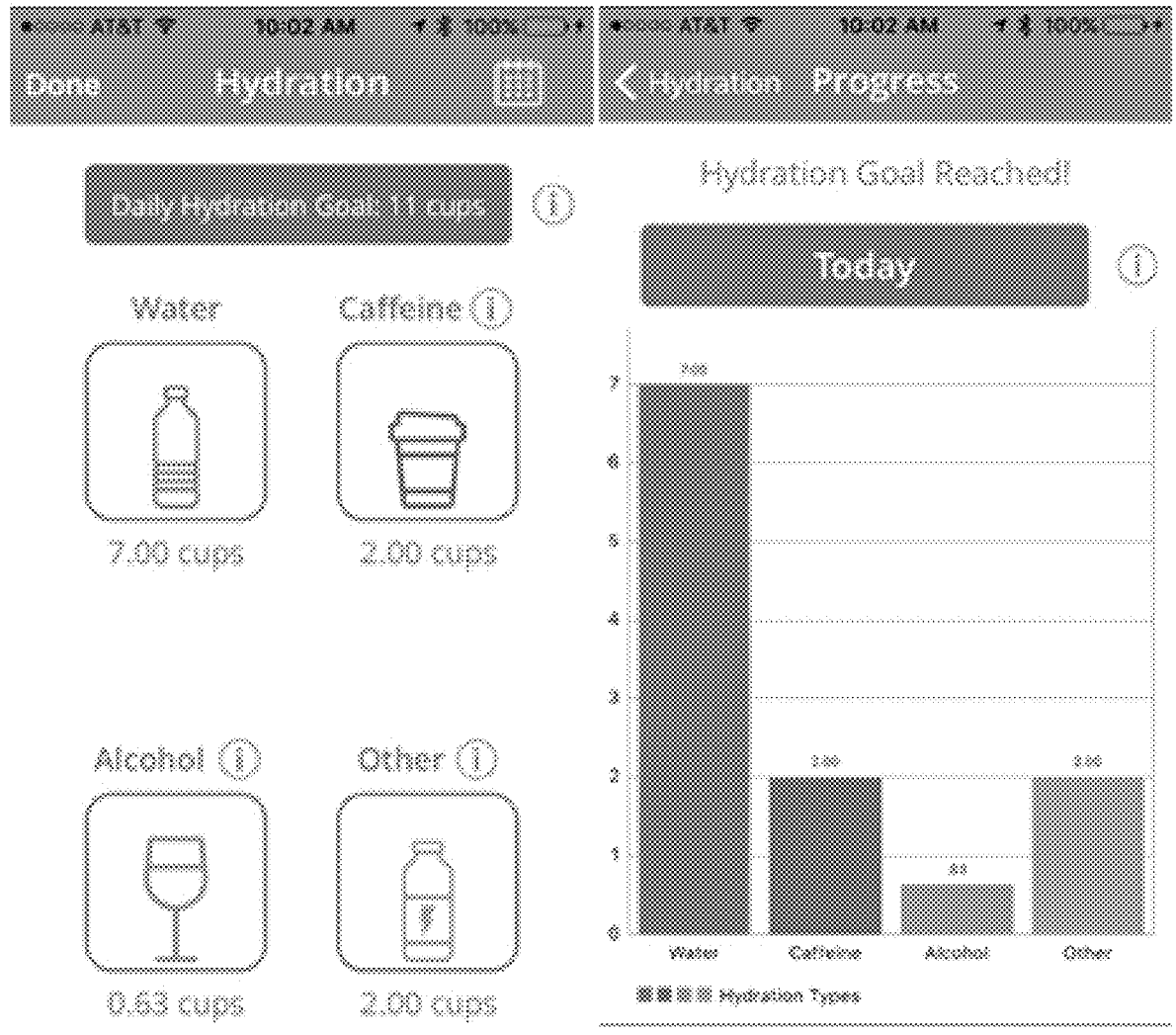
FIG. 3B illustrates example hydration monitoring interfaces.

Alerts associated with use of the ostomy device may include alerts related to dehydration, electrolyte imbalance, abnormally high or low parameters, such as stomal output, presence or absence of certain biomarkers, or skin irritation. The patient coach can forward such alerts to a clinician for further assistance. FIG. 3A illustrates an example patient care hydration monitoring process 300 through which an alert may be generated, and a patient coach may respond. The process can be implemented for any other parameters associated with use of the ostomy device. At block 310, a processor can determine patient intake through a tracker provided to the patient, such as a food and/or hydration tracker. An example tracker is illustrated in FIG. 3B. At block 312, the processor can monitor sensors associated with the ostomy device 102 ostomy bag hydration related information, such as the volume in the bag. At block 314, the processor can determine a hydration level using software and algorithms that analyze the patient intake data and the sensor data to determine a hydration level. At block 316, the processor can analyze the hydration level to determine if it falls below a threshold value. The threshold value may correspond to a value at which fluid loss exceeds fluid intake. In other embodiments, a threshold value may correspond to the point at which the patient would normally start to feel a disruption of metabolic processes due to fluid loss. In other embodiments, there may be more than one threshold value. For example, a first threshold value can correspond to low levels of hydration that would not yet medically qualify as dehydration and a second threshold value can correspond to medical dehydration. If the hydration level falls below a threshold value, the processor can trigger an alarm at block 318. Alternatively, if the hydration level does not fall below a threshold value, the system can continue monitoring the patient without triggering an alarm. Various protocols can be used to determine the hydration level. For example, extremely high output per day (such as greater than 1500 mL or 1800 mL per day) may indicate potential dehydration as the intestines are not absorbing water. Extremely low output per day may also indicate potential dehydration as the patient may not be drinking enough water.

Different alarms can be triggers when different threshold values are crossed. For example, an alarm due to the crossing of the first value can allow the patient coach to contact the patient to remind the patient to hydrate, and an alarm due to the crossing of the second value can allow the patient coach to request intervention by a clinician. The system can also optionally recommend to the patient the nearest hydration venue based on the patient's location, for example, a convenience store, restaurant, café, and the like. Different levels of clinician intervention can also optionally be present. For example, a nurse can communicate with the patient to remind the patient to hydrate in case of mild dehydration. In case of more severe dehydration, the clinician can dispatch medication and/or IV infusion to the patient (such as at the patient's home). In case of very severe dehydration, the patient coach and/or the clinician can dispatch a driver to pick up the patient and send the patient to an emergency room or clinic for treatment.

The alarm can be triggered on the user device 130 and a care provider device 160. The patient coach can contact the patient when an alert is triggered to determine if the alert is valid due to accurate patient intake information and whether further action, such as medical intervention, is necessary. If medical intervention is deemed necessary, the patient coach can direct the patient to seek immediate medical care, refer the patient to a clinician, and direct the patient to increase their intake of fluids so as to avoid further dehydration.

Advantageously, the patient coach's monitoring of the patient through the alert system can decrease patient hospital readmission. For example, dehydration is a common reason why patients are readmitted into the hospital in the first three months following an ostomy procedure and patient coaches can reduce occurrence and/or extent of dehydration before it becomes serious enough for immediate medical attention by directing a patient to the problem. Additionally, the patient coach serving as an interpreter of patient data at an early stage can reduce unnecessary medical intervention due to false alerts that may result from a malfunctioning ostomy device 102 or failure of the patient to accurately record data. Patient coaches serving in this function can also build a rapport with the patient, improving the patient experience, and use such contacts as a means to educate the patient about using the ostomy device 102 and properly caring for their stoma.

Another Example Patient Monitoring Process

Figure 3C:
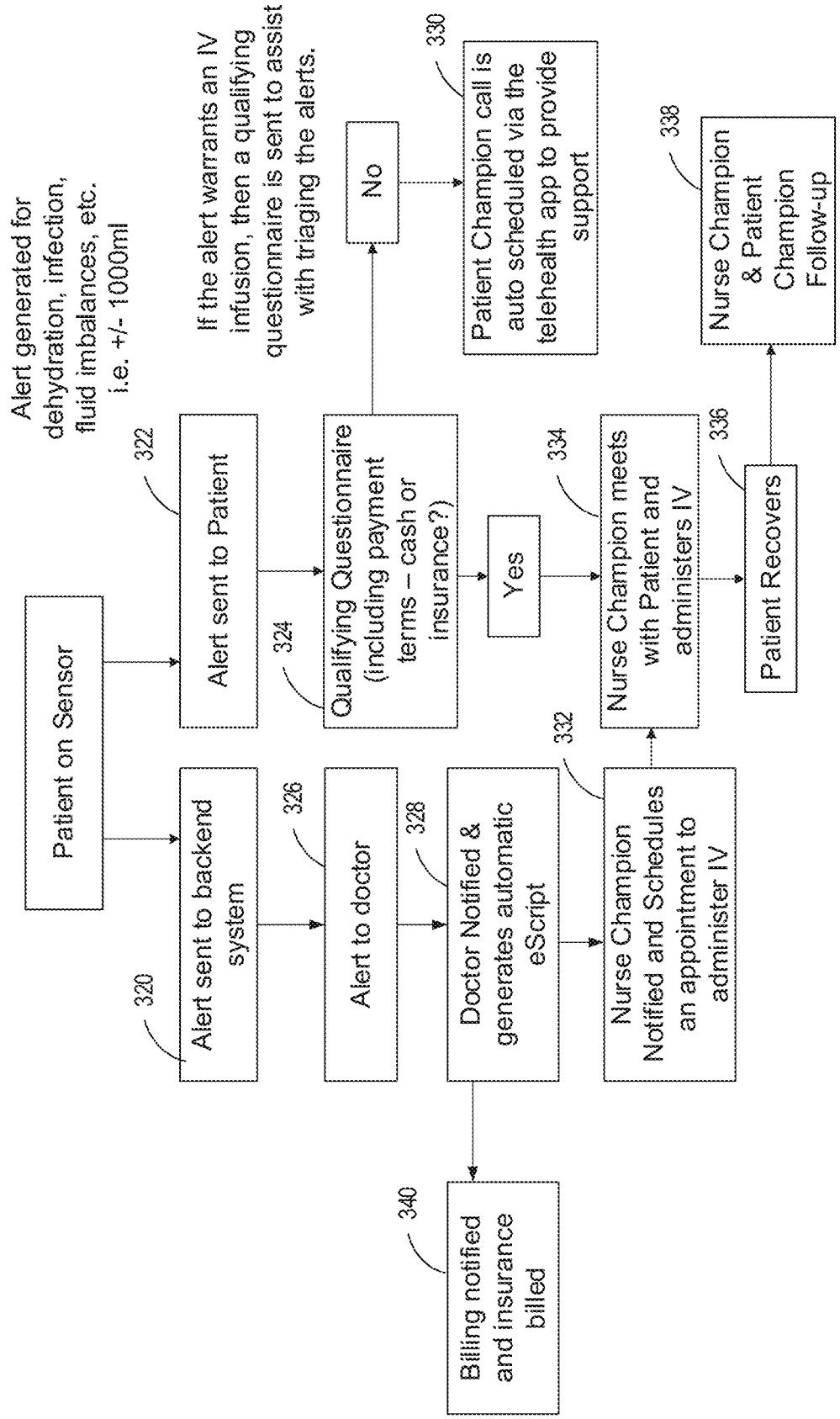
FIG. 3C illustrates an example patient care monitoring process.

FIG. 3C depicts an example process for monitoring a patient. The process can be implemented using aspects of the system shown in FIG. 1. The process of 3C depicts another example integration of a patient coach, a nurse, a doctor, and/or a manufacturer to provide support to the new patient using data from the ostomy bag sensor.

In the example process shown in 3C, a patient may be wearing an ostomy bag or wafer with a sensor, and an application (whether cloud-based or on a user device) may analyze data from the sensor(s) and output an alert. The alert may be an indication of dehydration, infection, fluid imbalance, a biomarker exceeding a threshold, or some other alert based in part on ostomy sensor output.

The application may provide a user interface that allows the user to track fluid (and/or solid) intake. The user interface may include, for instance, user interface controls (such as buttons, icons, text boxes, or the like) that enable a user to specify how much fluid intake the user has had. When the user drinks something, the user can input that the user has drunk something and indicate approximately how much the user drank. FIG. 3B illustrates example mobile application screens show how much the user has drunk during a day, as input into the application (a user can also select one of the icons in the left screenshot to input additional indications that fluid has been drunk and amounts):

Thus, the application can have an approximate indication of how much fluid and/or solid the user has consumed, and the application can have an indication of the output into the ostomy bag based on information obtained from the one or more sensors. The application can therefore take the difference between the output and the input to detect a fluid imbalance or dehydration.

The alert can be sent from the application over a network to the backend system at step 322 in FIG. 3C. Likewise, the patient can be informed of the alert on the patient's application (for example, on the user device) at step 320.

Following the left path in FIG. 3C, the alert can be sent to a doctor at a step 326, who may be notified and generate an automatic eScript (electronic prescription) for intravenous (IV) fluids or other forms of treatment (such as antibiotics, a new ostomy bag, and the like) at a step 328. The provider of the ostomy bag and/or application can be notified, and insurance can be billed at a step 340. Likewise, a nurse can be notified so that the nurse can schedule an appointment to administer an IV infusion to the patient at a step 332, if the doctor deemed an IV infusion necessary or desired. The patient coach can directly order delivery of fluid to the patient, such as for oral consumption in the case of more mild dehydration of the patient.

Following the right path in FIG. 3C, after the alert is sent to the patient at a step 322, optionally if the alert warrants an IV infusion, then a qualifying questionnaire can be sent to the patient to assist with triaging the alert at a step 324. The questionnaire may include questions designed to identify a seriousness of the patient's fluid imbalance or dehydration. More seriously dehydrated or imbalanced patients can be automatically prioritized by the backend system (see FIG. 1) to bring the more serious patients' alerts to the attention of a nurse or doctor before less serious alerts. In another example situation, the alert can include an indication of its seriousness based on the amount of fluid imbalance, with greater fluid imbalances leading to more serious alerts. Thus, the questionnaire may be omitted.

However, the questionnaire may also include payment terms, such as cash or insurance. If payment terms are not satisfied, the patient may still be connected with the patient coach or a call with the patient coach may be scheduled automatically via the application at a step 330. In that way, even patients that cannot afford an immediate IV infusion can receive support from the patient coach, following the patient coach example features discussed elsewhere herein.

If payment is satisfied, a nurse can meet with the patient and administer the IV infusion, if ordered by the doctor at a step 334. Nurses can be nurses who work with ostomy patients regularly and are experienced at assisting ostomy patients. A list of available nurses and their contact information can be accessible to the backend system.

Once the patient recovers at a step 336, the nurse and/or patient coach can follow up with the patient (e.g., using the telehealth feature of the application) to provide instruction, encouragement, and support at a step 338.

Example Patient Care Workflow

As part of providing care, care providers may be tasked with communicating with new ostomy patients. Care providers may contact the patients on a set schedule or as needed. For example, the care provider may contact the patient prior to the ostomy procedure to provide support to the patient prior to the procedure. For a period of time following the procedure, for example two months, the care provider may contact the patient on a weekly basis. After that initial period, the care provider may continue to contact the patient on a weekly basis or as needed depending on the patient's individual ability to adapt to their new lifestyle with a stoma. The communication schedule and the identity of the patient care provider may be altered based on patient need. The patient need may be determined by pre-determined critical intervals after the ostomy procedure, based on care provider determination, based on a computer algorithm, or by patient request. In other embodiments, the patient coach may determine that a patient needs more extensive emotional support than the patient coach can provide and arrange for a psychologist to contact the patient.

Figure 4:
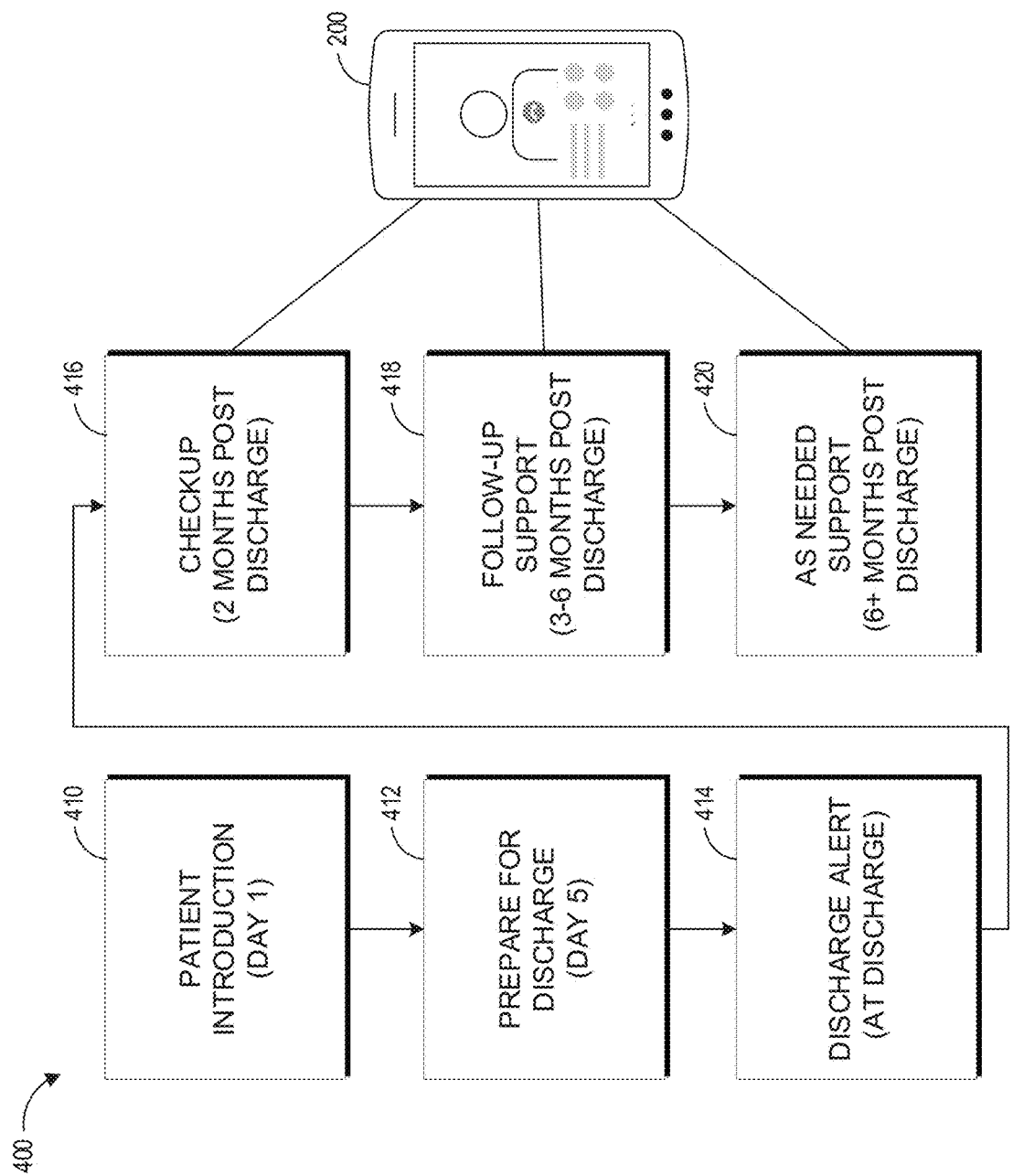
FIG. 4 depicts an example patient care workflow.

FIG. 4 depicts an example patient care workflow 400 according to the patient care systems and methods described herein. The workflow can be in addition to the patient coach program disclosed herein. This example workflow includes the following:

At block 410, corresponding to Day 1, a chronically ill or emergency patient may be introduced to at least one care provider such as a nurse and patient coach.

At block 412, while the patient remains in hospital and after discharge, which in one configuration may be about 5 days after surgery, an account manager may work with the hospital medical team to address any technical issues. The case manager may also inform the patient of how to access supplies of the smart bag, etc.

At block 414, corresponding to the period of time immediately after discharge, an example patient care and/or ostomy device provider may receive an alert that the patient has been discharged and verify with technical support that the ostomy device and patient care interface are connected properly.

At block 416, corresponding to the period of about 3 Months after discharge, a care provider, such as a patient coach may contact the patient using a patient care interface 200 3× a week for 2 months to provide support and education regarding lifestyle as an ostomate, hydration, food related issues, pain and stress management and check on the patient's well-being and potential complications such as dehydration and/or skin irritation and verify that the patient is using the sensor and tracker correctly. Additionally, the patient coach may request that another care provider, who may be a healthcare professional, to contact the patient using a patient care interface 200, for example, at least once a week for 2 months to provide emotional support, discuss the psychology of the situation.

At block 418, corresponding to the period of about 3-6 Months after discharge, care providers such as, a patient coach and/or a nurse (or any other healthcare professional) may contact the patient using a patient care interface 200 once every 2 weeks or as needed, providing support as needed.

At block 420, corresponding to the period of After 6 Months, care providers such as, a patient coach and/or a nurse (or any other healthcare professional) may contact the patient using a patient care interface 200 as needed, providing support as needed.

In addition to the set schedule, the patient may contact the patient coach (and other care providers through the patient coach) using the patient care interface 200 on demand as needed throughout the whole process.

Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms) Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a hardware processor comprising digital logic circuitry, a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth.

Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A method of remotely providing post-operative care to an ostomy patient, the method comprising:
using at least one hardware processor in communication with a non-transitory storage medium configured to store computer-executable instructions:
receiving and processing, over a network, ostomy data associated with use of an ostomy device by the ostomy patient;
transmitting, over the network, the processed ostomy data to an application configured to facilitate providing post-operative support to the ostomy patient;
receiving an input from the application in response to the processed ostomy data, wherein the input comprises responses automatically generated by an artificial intelligence service; and
transmitting the input to a patient device.

2. The method of claim 1, wherein the ostomy data further comprises patient input data or at least a stomal output measurement, or both.

3. The method of claim 2, further comprising generating a monitored value based on the ostomy data.

4. The method of claim 3, further comprising generating an alert if the monitored value exceeds or falls below a threshold value, wherein the processed ostomy data comprises the alert.

5. The method of claim 4, further comprising automatically transmitting a questionnaire to the ostomy patient in response to the alert and assessing a severity of the alert based at least in part on the ostomy patient's answer(s) to the questionnaire.

6. The method of claim 4, further comprising automatically prioritizing more severe alerts for attention of a care provider configured to be contacted via the application.

7. The method of claim 3, wherein the monitored value is indicative of an ostomy patient's hydration status.

8. The method of claim 1, wherein the artificial intelligence service is activated in response to a human patient coach being unavailable to review the ostomy data at the application.

9. The method of claim 1, wherein the artificial intelligence service is trained to answer questions related to use of the ostomy device.

10. The method of claim 9, wherein the artificial intelligence service is equipped with natural language processing.

11. A system configured to remotely provide post-operative care to an ostomy patient, the method comprising:
   a non-transitory storage medium configured to store computer-executable instructions; and
   at least one hardware processor in communication with the non-transitory storage medium, wherein the at least one hardware processor is configured to:
   receive and process, over a network, ostomy data associated with use of an ostomy device by the ostomy patient;
   transmit, over the network, the processed ostomy data to an application configured to facilitate providing post-operative support to the ostomy patient;
   receive an input from the application in response to the processed ostomy data, wherein the input comprises responses automatically generated by an artificial intelligence service; and
   transmit the input to a patient device.

12. The system of claim 11, wherein the ostomy data further comprises patient input data or at least a stomal output measurement, or both.

13. The system of claim 12, wherein the at least one hardware processor is configured to generate a monitored value based on the ostomy data.

14. The system of claim 13, wherein the at least one hardware processor is further configured to generate an alert if the monitored value exceeds or falls below a threshold value, wherein the processed ostomy data comprises the alert.

15. The system of claim 14, wherein the at least one hardware processor is further configured to automatically transmit a questionnaire to the ostomy patient in response to the alert and assess a severity of the alert based at least in part on the ostomy patient's answer(s) to the questionnaire.

16. The system of claim 14, wherein the at least one hardware processor is further configured to automatically prioritize more severe alerts for attention of a care provider configured to be contacted via the application.

17. The system of 13, wherein the monitored value is indicative of an ostomy patient's hydration status.

18. The system of claim 11, wherein the artificial intelligence service is activated in response to a human patient coach being unavailable to review the ostomy data at the application.

19. The system of claim 11, wherein the artificial intelligence service is trained to answer questions related to use of the ostomy device.

20. The system of claim 19, wherein the artificial intelligence service is equipped with natural language processing.

* * * * *